US009932618B2

United States Patent
Lee et al.

(10) Patent No.: US 9,932,618 B2
(45) Date of Patent: Apr. 3, 2018

(54) CONTINUOUS PRODUCTION METHOD OF ADENOSINE TRIPHOSPHATE AND NICOTINAMIDE ADENINE DINUCLEOTIDE (PHOSPHATE) USING PHOTOSYNTHETIC MEMBRANE VESICLE

(71) Applicant: SOGANG UNIVERSITY RESEARCH FOUNDATION, Seoul (KR)

(72) Inventors: Jeong Kug Lee, Seoul (KR); Eui Jin Kim, Seoul (KR)

(73) Assignee: Sogang University Research Foundation, Seoul (KR)

(*) Notice: Subject to any disclaimer, the term of this patent is extended or adjusted under 35 U.S.C. 154(b) by 0 days.

(21) Appl. No.: 15/113,697

(22) PCT Filed: Jan. 26, 2015

(86) PCT No.: PCT/KR2015/000783
§ 371 (c)(1),
(2) Date: Jul. 22, 2016

(87) PCT Pub. No.: WO2015/111972
PCT Pub. Date: Jul. 30, 2015

(65) Prior Publication Data
US 2017/0009268 A1    Jan. 12, 2017

(30) Foreign Application Priority Data
Jan. 27, 2014  (KR) .................. 10-2014-0009820

(51) Int. Cl.
C12N 1/20 (2006.01)
C12P 19/36 (2006.01)
(Continued)

(52) U.S. Cl.
CPC ............... *C12P 19/36* (2013.01); *C12N 1/12* (2013.01); *C12N 1/20* (2013.01); *C12N 13/00* (2013.01); *C12P 19/32* (2013.01)

(58) Field of Classification Search
CPC .................................... C12N 1/20; C12N 1/12
See application file for complete search history.

(56) References Cited

U.S. PATENT DOCUMENTS 5,500,086 A    3/1996  Sakai et al.
6,416,993 B1 *  7/2002  Wexler .............. C02F 3/32
                                                                210/601
(Continued)

FOREIGN PATENT DOCUMENTS

KR    1020110028853 A    3/2011

OTHER PUBLICATIONS

International Search Report for PCT/KR2015/000783 dated Jul. 17, 2015, 4 pages.
(Continued)

*Primary Examiner* — Rosanne Kosson
(74) *Attorney, Agent, or Firm* — Lathrop Gage LLP

(57) ABSTRACT

The present invention relates to a composition for production of photosynthetic light-reaction products comprising photosynthetic membrane vesicles, and a production method for the photosynthetic light-reaction products by using the composition. In addition, the present invention relates to a preparation method for a photosynthetic light-reaction monomer comprising a step of isolating vesicles from the cell membrane of photosynthetic bacteria or algae.

18 Claims, 5 Drawing Sheets

(51) Int. Cl.
*C12N 1/12* (2006.01)
*C12P 19/32* (2006.01)
*C12N 13/00* (2006.01)

(56) References Cited

U.S. PATENT DOCUMENTS

2011/0008867 A1* 1/2011 Zarur ..................... C12N 9/00
                                                      435/189
2011/0244524 A1* 10/2011 Laible .................. C07K 14/245
                                                      435/91.5

OTHER PUBLICATIONS

Vermeglio et al., "Connectivity of the intracytoplasmic membrane of *Rhodobacter sphaeroides*: a functional approach", Photosynth Res (2016) 127:13-24.

Scheuring et al. "The architecture of Rhodobacter sphaeroides chromatophores" Biochimica et Biophysica Acta 1837 (2014): 1263-1270.

* cited by examiner

CONTINUOUS PRODUCTION METHOD OF ADENOSINE TRIPHOSPHATE AND NICOTINAMIDE ADENINE DINUCLEOTIDE (PHOSPHATE) USING PHOTOSYNTHETIC MEMBRANE VESICLE

CROSS-REFERENCE TO RELATED APPLICATION

This application claims priority to and is a 35 U.S.C. § 371 national phase application of PCT/KR2015/000783 (WO2015/111972), filed on Jan. 26, 2015 entitled "Continuous production method of adenosine triphosphate and nicotinamide adenine dinucleotide (phosphate) using photosynthetic membrane vesicle", which application claims priority to and the benefit of Korean Patent Application No. 10-2014-0009820, filed Jan. 27, 2014; the disclosures of which is incorporated herein by reference in their entirety.

TECHNICAL FIELD

The present invention relates to a composition containing a photosynthetic membrane vesicle for producing a product of the light-dependent reactions in photosynthesis and a method of continuously producing a product of the light-dependent reactions in photosynthesis using the composition.

BACKGROUND ART

The structure of modern industry has no choice but to be dependent on fossil fuels as most of the raw materials and energy sources in chemical engineering. The amount of fossil fuels is limited, and the use of fossil fuels causes various environmental problems as well as an economical problem. In such situations, research on novel renewable energy that can substitute for fossil fuels is progressing, and energy-generating technology using solar light corresponds to one of the ultimate energy technologies on which a human should depend. Light energy utilization, which is technology to convert light into chemical or electrical energy, can be implemented using various methods, and among these, in vivo photosynthesis has ended up with a current capability to utilize light after 3.5 billion-years of evolution.

Photosynthesis takes place in algae and various microorganisms as well as plants. Such photosynthesis is broadly classified into oxygenic photosynthesis and anoxygenic photosynthesis depending on the type of electron donor. The oxygenic photosynthesis takes place in plants, algae, cyanobacteria, etc., and is characterized by generating oxygen from water ($H_2O$) as an electron donor. Such oxygenic photosynthesis occurs in a thylakoid membrane, which is a distinct membrane structure present in microorganism and chloroplast of plants and algae. Light energy excites electrons to induce a series of electron flow, and during such electron flow, protons are transferred through the membrane to form a proton concentration gradient between the inner and outer spaces of the membrane. As a result, the proton concentration gradient leads to the synthesis of adenosine triphosphate (ATP) through the action of ATP synthase. Also, such an electron flow is transferred to ferredoxin, and finally reduces nicotinamide adenine dinucleotide phosphate ($NADP^+$) into a reduced form of nicotinamide adenine dinucleotide phosphate (NADPH). Here, the generated NADPH may be converted into a reduced form of nicotinamide adenine dinucleotide (NADH) by the action of pyridine nucleotide transhydrogenase (Pnt).

Anoxygenic photosynthesis is known to take place in purple non-sulfur bacteria, purple sulfur bacteria, green non-sulfur bacteria, green sulfur bacteria and Heliobacteria, and does not generate molecular oxygen during this process, unlike the oxygenic photosynthesis. Particularly, in purple non-sulfur bacteria, such a photosynthesis mechanism occurs in an intracytoplasmic membrane which is invaginated into the cell. In a reaction center present in the intracytoplasmic membrane of the bacteria, a photochemical reaction is initiated by light energy, thereby inducing cyclic electron transfer. ATP is synthesized from adenosine diphosphate (ADP) and inorganic phosphate by ATP synthase using a proton concentration gradient generated in this process as a driving force. However, when reverse electron flow in which protons are transferred in an opposite direction of the intracytoplasmic membrane takes place by complex I present therein, adenine dinucleotide ($NAD^+$) is reduced into NADH. Afterward, quinone which has lost electrons obtains electrons again during the conversion of succinate into fumarate by the action of succinate dehydrogenase (complex II) also present in the intracytoplasmic membrane. NADH generated by such a mechanism may be converted into NADPH by the action of a pyridine nucleotide transhydrogenase like in oxygenic photosynthesis.

ATP and NAD(P)H serve as cofactors of enzymes mediating various in vivo biochemical reactions. Thus, in living body, continuous synthesis of ATP and NAD(P)H is needed, and enzyme reactions for producing such cofactors by consuming energy from various metabolic substances have been known. As representative examples, ATP and NADH are generated by the action of the related enzymes in glycolysis and citric acid (or TCA) cycle. Moreover, methods of synthesizing ATP and NAD(P)H for in vitro biochemical reactions have been known. For ATP synthesis, methods using creatine phosphate and creatine phosphokinase are known. Creatine phosphokinase mediates a reaction for ATP synthesis by transferring a phosphate group of the creatine phosphate to ADP. That is, this enzyme may synthesize ATP from ADP by consuming the creatine phosphate. Also, glucose-6-phosphate dehydrogenase mediates the reduction of $NADP^+$ into NADPH by consumption of glucose-6-phosphate. However, when such reactions are practically applied to an in vitro enzyme reaction for producing a useful substance, the creatine phosphate or glucose-6-phosphate has to be continuously provided during reaction, resulting in a greatly increase of production cost with low practicality.

The invention disclosed in Korean Patent Application No. 10-2011-7017135 proposes that a separated composition for regenerating ATP may include a thylakoid membrane. However, for photophosphorylation in the thylakoid membrane to generate ATP, a proton concentration gradient is necessarily formed, and it may not be accomplished with a planar membrane, which is not a vesicle-type membrane by which inner and outer spaces are spatially separated. Actually, the above application does not present the result of generating ATP using the thylakoid membrane. Also, the above invention does not present a method of producing NAD(P)H using the thylakoid membrane, either.

In addition, the invention disclosed in Korean Patent Application No. 10-2008-0021127 is similar to the present invention in terms of the use of separated thylakoid membrane as an active component, but is different in that the invention is mainly characterized by presenting a method of controlling obesity by making a human feel satiety with an inhibitory component of thylakoid membrane against a pancreatic lipase.

The things that are described as the background art are merely provided to help in understanding the background of the present invention, and thus it should not be taken as an admission that they correspond to the conventional art previously known to those of ordinary skill in the art.

DISCLOSURE

Summary of the Invention

Technical Problem

The inventors had attempted to find a method of continuously producing products of the light-dependent reactions in photosynthesis such as ATP and NAD(P)H using photosynthetic bacteria such as cyanobacteria or purple non-sulfur bacteria or algae. As a result, the inventors identified that, when a photosynthetic light reaction-performing apparatus is constructed by separating only vesicles from cell membranes of the bacteria or algae, the products of the light-dependent reactions in photosynthesis can be continuously generated in the presence of electron donor, and thus completed the present invention.

Therefore, an objective of the present invention is directed to provide a composition for producing a product of the light-dependent reactions in photosynthesis, which contains a photosynthetic membrane vesicle.

Another objective of the present invention is directed to providing a light-dependent reaction-performing unit, which includes the composition for producing a product of the light-dependent reactions in photosynthesis.

Still another objective of the present invention is directed to providing a method of preparing the light-dependent reaction-performing unit, which includes isolating a photosynthetic membrane vesicle.

Yet another objective of the present invention is directed to providing a method of producing the product of the light-dependent reactions in photosynthesis, which includes applying light to a photosynthetic membrane vesicle.

Other objectives and advantages of the present invention will be explained clearly by the detail description, claims, and drawing of the present invention.

Technical Solution

According to an aspect of the present invention, the present invention provides a composition containing a photosynthetic membrane vesicle to produce a product of the light-dependent reactions in photosynthesis.

According to another aspect of the present invention, the present invention provides a method of producing a product of the light-dependent reactions in photosynthesis, which includes applying light to a photosynthetic membrane vesicle.

The inventors had attempted to find a method of continuously producing products of the light-dependent reactions in photosynthesis such as ATP and NAD(P)H using photosynthetic bacteria such as cyanobacteria, purple non-sulfur bacteria, or algae. As a result, the inventors identified that, when a photosynthetic light reaction-performing apparatus is constructed by separating only vesicles from cell membranes of the bacteria or algae, the products of the light-dependent reactions in photosynthesis can be continuously generated in the presence of electron donor.

The term "photosynthetic membrane vesicle" used herein refers to a cell membrane-protein complex that can be separated from photosynthetic bacteria or algae capable of performing photosynthesis using light energy in the form of a vesicle, and capable of performing the light-dependent reactions in photosynthesis under appropriate light irradiation.

The term "photosynthetic bacteria" used herein refers to bacteria capable of performing photosynthesis using light energy, and may be broadly classified into oxygenic photosynthetic bacteria and anoxygenic photosynthetic bacteria depending on the type of electron donor.

Oxygenic photosynthesis is characterized by generating oxygen from water ($H_2O$) as an electron donor, representatively in algae or cyanobacteria. Algae or cyanobacteria have a thylakoid membrane (TM), which is a specific cell membrane structure that performs photosynthesis.

The term "thylakoid membrane vesicle" used herein refers to a cell membrane unit including two types of photosystems and many proteins that transport electrons. The thylakoid membrane vesicle has an ability to produce ATP and NADPH using light energy unlike a typical membrane vesicle from non-photosynthetic bacteria.

According to an exemplary embodiment of the present invention, cyanobacteria capable of obtaining the thylakoid membrane vesicle are selected from the group consisting of *Synechocystis* sp., *Synechococcus* sp., *Nostoc* sp., *Anabaena* sp., *Gloeobacter* sp. and *Cyanobacterium* sp.

Anoxygenic photosynthesis is characterized by oxygen not being generated in photosynthesis, representatively, in purple non-sulfur bacteria, purple sulfur bacteria, green non-sulfur bacteria, green sulfur bacteria and Heliobacteria. Particularly, in the purple non-sulfur bacteria, the photosynthesis mechanism takes place in an intracytoplasmic membrane (ICM) furrowed into the cell.

The term "intracytoplasmic membrane vesicle" used herein refers to a cell membrane unit of the intracytoplasmic membrane, which includes a reaction center, a light harvesting complexes and a number of proteins that transport electrons. The intracytoplasmic membrane vesicle, unlike a typical cell membrane vesicle, can produce ATP and NADH using light energy.

According to an exemplary embodiment of the present invention, purple non-sulfur bacteria from which the intracytoplasmic membrane vesicle can be obtained are selected from the group consisting of *Rhodobacter* sp., *Rhodospirillum* sp., *Rhodopseudomonas* sp., *Roseobacter* sp., *Bradyrhizobium* sp., and *Rubrivivax* sp.

The *Rhodobacter* sp. purple non-sulfur bacteria include *Rhodobacter capsulatus, Rhodobacter apigmentum, Rhodobacter aestuarii, Rhodobacter blasticus, Rhodobacter changlensis, Rhodobacter azotoformans, Rhodobacter ovatus, Rhodobacter gluconicum, Rhodobacter johrii, Rhodobacter litoralis, Rhodobacter maxis, Rhodobacter megalophilus, Rhodobacter vinaykumarii, Rhodobacter viridis, Rhodobacter massiliensis, Rhodobacter denitrificans*, and *Rhodobacter veldkampii* as well as *Rhodobacter sphaeroides*.

The *Rhodospirillum* sp. purple non-sulfur bacteria include *Rhodospirillum centenum, Rhodospirillum indiensis, Rhodospirillum oryzae, Rhodospirillum photometricum, Rhodospirillum molischianum*, and *Rhodospirillum sulfurexigens* as well as *Rhodospirillum rubrum*.

The *Rhodopseudomonas* sp. purple non-sulfur bacteria include *Rhodopseudomonas acidopilia, Rhodopseudomonas boonkerdii, Rhodopseudomonas faecalis, Rhodopseudomonas harwoodiae, Rhodopseudomonas julialichen, Rhodopseudomonas oryzae, Rhodopseudomonas pangongensis, Rhodopseudomonas pentothenatexigens, Rhodopseudomonas rhenobacensis, and *Rhodopseudomonas thermotolerans* as well as *Rhodopseudomonas palustris*.

The *Roseobacter* sp. purple non-sulfur bacteria include *Roseobacter litoralis*, *Roseobacter prionitis* as well as *Roseobacter denitrificans*.

In addition, the *Rubrivivax* sp. purple non-sulfur bacteria include *Rubrivivax gelatinosus*.

The term "product of the light-dependent reactions in photosynthesis" used herein refers to a product produced by the light-dependent reactions of photosynthetic bacteria or algae for converting light into chemical energy, and the product includes one or more light reaction products selected from the group consisting of ATP, NADH and NADPH.

The present invention is designed to prepare a photosynthetic light reaction performing unit, separate from the photosynthetic bacteria, as an energy generating unit for generating the products of the light-dependent reactions in photosynthesis such as ATP and NAD(P)H for various biochemical reactions, when a thylakoid membrane vesicle and an intracytoplasmic membrane vesicle are obtained, and then the light-dependent reactions using the separated photosynthesis-specific cell membrane vesicles are allowed to be performed in vitro.

In the present invention, conditions for photosynthesis are those that induce the light-dependent reactions of photosynthetic bacteria, and include appropriate light (wavelength and intensity), temperature and an air composition, and one of ordinary skill in the art may determine optimal conditions according to a specific type of photosynthetic bacteria. For example, the photosynthesis of algae or cvyanobacteria may be performed at a temperature of approximately 20 to 37° C. under an anaerobic or aerobic condition using light with an intensity of approximately 5 to 500 micro Einstein/$m^2 \cdot s$ (μmole photons/$m^2 \cdot s$), and preferably, at a wavelength of 400 to 700 nm. To satisfy such a wavelength range, fluorescent light and LED light may be used as light sources. In an exemplary embodiment, the photosynthesis of cyanobacteria is performed with white light (fluorescent light) at an intensity of 50 micro Einstein/$m^2 \cdot s$ under an aerobic condition at 30° C. The photosynthesis of purple non-sulfur bacteria may also be performed at approximately 20 to 37° C. under an anaerobic or microaerobic condition using light with an intensity of approximately 3 to 300 Watts/$m^2$ and preferably at a wavelength of 350 to 1000 nm. Here, the microaerobic condition may be defined as a condition in which the partial pressure of oxygen is within 5%. To satisfy such a wavelength range, incandescent light and halogen light may be used as light sources. In another exemplary embodiment, the photosynthesis of purple non-sulfur bacteria is performed with light at an intensity of 15 Watts/$m^2$ light under an anaerobic condition at 30° C.

The thylakoid membrane vesicle including a light reaction apparatus of cyanobacteria or algae can generate a proton concentration gradient between inner and outer spaces of the membrane due to electron transport using light energy, and convert ADP and inorganic phosphate into ATP by the action of ATP synthase using kinetic energy derived from the concentration gradient as a driving force. Also, in the reaction centers of purple non-sulfur bacteria, a photochemical reaction is induced by light energy, thereby inducing cyclic electron transfer and synthesizing ATP by ATP synthase using the proton concentration gradient generated thereby as a driving force. FIG. 1 shows the result of measuring the efficiency of synthesizing ATP using the separated thylakoid membrane vesicle and intracytoplasmic membrane vesicle. In a dark condition in which light is not given to the two types of cell membrane vesicles, ATP synthesis rate is lower than that in a light condition in which light is provided, and based on the above result, it may be determined that the majority of ATP generated by light is a product of the light-dependent reaction in photosynthesis.

In the present application, the optimal concentrations of the thylakoid membrane vesicle and intracytoplasmic membrane vesicle for producing ATP through a light reaction were examined. To this end, the thylakoid membrane vesicle was quantified based on the concentration of chlorophyll a (Chl a), and the intracytoplasmic membrane vesicle was quantified based on the concentration of bacteriochlorophyll a (Bchl a).

The concentration of chlorophyll a in the vesicle separated from the thylakoid membrane of algae or cyanobacteria may be 1 μg chlorophyll a/ml to 1 mg chlorophyll a/ml, and preferably 5 μg chlorophyll a/ml to 200 μg chlorophyll a/ml. When the concentration of chlorophyll a is less than the above range, photosynthesis is not sufficiently performed, and ATP and NAD(P)H are produced at a low rate. When the concentration of chlorophyll a is more than the above range, due to limited light permeability, ATP and NAD(P)H production efficiency is not increased anymore and saturated.

Also, the concentration of bacteriochlorophyll a in the vesicle separated from the intracytoplasmic membrane of the purple non-sulfur bacteria is 1 μg bacteriochlorophyll a/ml to 1 mg bacteriochlorophyll a/ml, and preferably 5 μg bacteriochlorophyll a/ml to 200 μg bacteriochlorophyll a/ml. When the concentration of bacteriochlorophyll a is less than the above range, photosynthesis is not sufficiently performed, and thus ATP and NAD(P)H are produced at a low rate. When the concentration of bacteriochlorophyll a is more than the above range, due to limited light permeability, ATP and NAD(P)H production efficiency is not increased anymore and thus saturated.

FIG. 2 shows ATP synthesis efficiency according to the concentrations of added thylakoid membrane vesicles and intracytoplasmic membrane vesicles, the concentrations being determined by the above method. As a result, in both of the cell membrane vesicles, ATP synthesis rates were increased according to the concentrations of the added vesicles, and it was shown that the ATP synthesis rate was saturated over certain level of vesicles. This means that, because of the light absorbing property of a photosynthetic apparatus, light permeability is decreased in the presence of a high concentration of the photosynthetic apparatuses, and thus the use of the photosynthetic membrane vesicles higher than a suitable concentration may be ineffective. Since the optimal concentration of use of the photosynthetic membrane vesicle is also increased in proportion to the relative light intensity, taking into account the condition for providing light energy according to the purpose of research and development, the optimal concentration of the photosynthetic membrane vesicle may be determined and applied by one or ordinary skill in the art.

According to an exemplary embodiment of the present invention, the composition of the present invention includes both of the vesicle separated from the thylakoid membrane of algae or cyanobacteria and the vesicle separated from the intracytoplasmic membrane of purple non-sulfur bacteria.

Since the thylakoid membrane vesicle and the intracytoplasmic membrane vesicle have different absorption wavelengths, the range of light energy that is not absorbed by one type of vesicle is absorbed by the other type of vesicle. Therefore, when a light reaction is induced using both types of photosynthetic membrane vesicles at the same time, ATP may be synthesized in a limited space with a relatively higher efficiency. FIG. 3 shows the ATP synthesis efficiency measured when ATP is produced only using the intracytoplasmic membrane vesicle and when ATP is generated using both the thylakoid membrane vesicle and the intracytoplasmic membrane vesicle based on the above-described expectation. As a result, when the two types of photosynthetic membrane vesicles are added, the ATP synthesis efficiency is higher. This means that, since the two types of photosynthetic membrane vesicles only absorb light at different wavelengths, when two types of photosynthetic membrane vesicles are simultaneously applied, rather than the use of a high concentration of one type of photosynthetic membrane vesicle, more effective ATP synthesis may occur.

Therefore, when the composition of the present invention includes both the vesicle separated from thylakoid membrane of algae or cyanobacteria and the vesicle separated from intracytoplasmic membrane of purple non-sulfur bacteria, light in different ranges of wavelengths, for example, light in the visible and infrared wavelength ranges are simultaneously absorbed, thereby producing the products of the light-dependent reactions in photosynthesis with the highest efficiency.

Electron flow taking place in the thylakoid membrane vesicle during photosynthesis results in generation of NADPH by reduction of $NADP^+$. The NADPH generated thereby may be converted into NADH by the action of pyridine nucleotide transhydrogenase (Pnt), which is a membrane protein. To examine whether the separated thylakoid membrane vesicle enables reduction to NADH and NADPH as well as synthesis of ATP when light is applied, efficiency of reduction to NADH and NADPH was measured. Experiments were conducted by adding only NADP to a reaction solution containing the thylakoid membrane vesicle in order to measure the NADPH synthesis efficiency, and by adding both of NAD and NADP to the reaction solution containing the thylakoid membrane vesicle in order to measure the NADH synthesis efficiency. FIG. 4 shows the NADH and NADPH synthesis efficiency in the thylakoid membrane vesicle determined by the application of light. As a result, NADH and NADPH synthesis rates under the dark condition are considerably lower than those under the light condition, and it can be seen from the above result that most of the generated NADH and NADPH are products of the light-dependent reaction in photosynthesis using the light. Referring to FIG. 4, since the NADPH production efficiency is higher than that of NADH, a light reaction unit composed of only the thylakoid membrane vesicle may be the most suitably applied to induce a biosynthetic reaction that consumes ATP and NADPH. Since NADH may also be generated by the action of the nucleotide transhydrogenase of the thylakoid membrane vesicle, a method of improving the NADH production efficiency may also be accomplished by various additional attempts to increase the nucleotide transhydrogenase activity.

In the intracytoplasmic membrane, unlike the thylakoid membrane, it is known that NADH is mainly produced in photosynthesis. In addition, the generated NADH may be converted into NADPH by the action of pyridine nucleotide transhydrogenase (Pnt), which is a membrane protein. To investigate whether the separated intracytoplasmic membrane vesicle enables reduction to NADH and NADPH as well as ATP synthesis activity under a light condition, efficiency of reduction to NADH and NADPH was examined. To measure NADH synthesis efficiency, only succinate and $NAD^+$ were added to a reaction solution, but to measure the NADPH synthesis efficiency, all of succinate, $NAD^+$ and $NADP^+$ were added. FIG. 5 shows the result of measuring NADH and NADPH synthesis efficiency in the intracytoplasmic membrane vesicle. The NADH and NADPH synthesis rates under the dark condition are considerably lower than those under the light condition, and thus it can be identified that most of the synthesized NADH and NADPH are products of the light-dependent reaction in photosynthesis using the light. In the intracytoplasmic membrane vesicle, as expected, the NADH production efficiency is relatively higher than that of NADPH, and thus when the light reaction unit is constructed only with the intracytoplasmic membrane vesicle, it is concluded that the light reaction unit can be useful in induction of biosynthetic reaction that consumes ATP and NADH.

However, in the generation of NAD(P)H in the intracytoplasmic membrane vesicle, the use of succinate as an electron donor is required, in contrast with the ability of the thylakoid membrane vesicle to continuously produce NAD(P)H by obtaining electrons from water in an aqueous solution without the input of foreign substances. Therefore, for ATP synthesis, both of the thylakoid membrane vesicle and the intracytoplasmic membrane vesicle may be used without a significant difference, but for NAD(P)H production, a method of employing the thylakoid membrane vesicle may be more efficient. However, since the thylakoid membrane vesicle and the intracytoplasmic membrane vesicle have different absorption wavelengths, when the two types of photosynthesis-specific cell membrane vesicles are used together to induce the light reaction, a higher efficiency may be exhibited in a limited space. When succinate is not added to a reaction solution containing both of the thylakoid membrane vesicle and the intracytoplasmic membrane vesicle, the thylakoid membrane vesicle may generate ATP and NAD(P)H, and the intracytoplasmic membrane vesicle may generate only ATP. Therefore, based on the information provided in the present application, one of ordinary skill in the art can determine whether the thylakoid membrane vesicle and the intracytoplasmic membrane vesicle may be added individually or simultaneously, depending on the purpose of research and development.

According to still another aspect of the present invention, the present invention provides a light-dependent reaction-performing unit including the composition for producing a product of the light-dependent reactions in photosynthesis.

The term "light-dependent reaction-performing unit" used herein is one unit of an apparatus or device capable of performing the light-dependent reactions in photosynthesis separately from the photosynthetic bacteria or algae, the unit including a composition containing the photosynthetic membrane vesicle, preferably, one or more separated vesicles selected from the group consisting of a thylakoid membrane vesicle and an intracytoplasmic membrane vesicle. Combination of such units may constitute one large assembly.

According to an exemplary embodiment of the present invention, the present invention relates to a method of producing a product of the light-dependent reactions in photosynthesis using a photosynthetic membrane vesicle, the method including the following steps:

a) separating a vesicle from one or more cell membranes selected from the group consisting of a thylakoid membrane of photosynthetic bacteria or algae, preferably, cyanobacteria or algae and an intracytoplasmic membrane of purple non-sulfur bacteria;

b) constructing a light-dependent reaction-performing unit including the separated vesicle; and c) producing a product of the light-dependent reactions in photosynthesis by applying light to the light-dependent reaction-performing unit.

The light-dependent reaction-performing unit may be prepared by simply liberating the obtained vesicles in an aqueous solution, which may only exhibit a temporary effect. According to the method, a corresponding product may be accumulated in the reaction solution, and while retrieving the product, the structure and function of the vesicle included in the light reaction unit may be damaged, and therefore, it cannot be the most preferable configuration. Thus, by using various types and shapes of membranes such as a dialysis membrane or filter membrane having a smaller pore size than the thylakoid membrane vesicle and intracytoplasmic membrane vesicle to prepare the unit with either the obtained thylakoid membrane vesicle or intracytoplasmic membrane vesicle or the combination thereof, a product of the light-dependent reactions in photosynthesis that is smaller than the vesicles passes through a pore of the dialysis membrane or filter membrane, thereby obtaining the product of the light-dependent reactions in photosynthesis without damage to the structure and function of the vesicle. Since the vesicle separated from the thylakoid membrane of cyanobacteria or algae and the vesicle separated from the intracytoplasmic membrane of purple non-sulfur bacteria may have a diameter of 1 to 500 nm, and preferably 10 to 200 nm, a dialysis membrane or filter membrane which has a smaller pore size than the above vesicle may be useful.

In addition, to form a column-shaped reaction vessel, a planar membrane may be employed, and to form a three-dimensional reaction vessel, a spatial membrane may be employed. Also, to prepare the light reaction unit with either the thylakoid membrane vesicle or the intracytoplasmic membrane vesicle or the combination thereof, along with modifying of a chemical substance such as plastic or vinyl, a nano-scale lattice structure for preparing the light reaction unit by fixing the thylakoid membrane vesicle and the intracytoplasmic membrane vesicle to the inside thereof can be used. Moreover, as a material capable of binding to one or more of the lipids or membrane proteins present on the surfaces of the thylakoid membrane vesicle and the intracytoplasmic membrane vesicle is attached to the surface of a specific part in the construction of a reaction vessel, the light reaction unit can be prepared by fixing the thylakoid membrane vesicle and the intracytoplasmic membrane vesicle.

According to yet another aspect of the present invention, the present invention provides a method of preparing a light-dependent reaction-performing unit, the method including separating a vesicle from photosynthetic bacteria or algae.

The separation of a vesicle may include disrupting the photosynthetic bacteria or algae and separating a vesicle from the disrupted result.

In the present invention, to separate the thylakoid membrane vesicle and the intracytoplasmic membrane vesicle from cultured photosynthetic bacteria or algae, there is no particular limitation to the method of disrupting cells, but a physical method for minimizing the damage of a photosynthesis-specific cell membrane is preferably used. Specifically, a disruption method using powerfully mixture of glass beads, a disruption method using ultrasonic waves (sonication), and a disruption method using high-pressure injection (using a French Press) are preferably used. However, a chemical method for disrupting cells using a detergent such as SDS or an organic solvent such as chloroform is not preferable because it can cause damage to the structure and function of the vesicle membrane.

In the present invention, following the disruption of the photosynthetic bacteria or algae, as a method of separating the thylakoid membrane vesicle and the intracytoplasmic membrane vesicle, but not particularly limited to, centrifugation using a sucrose density gradient may be used, resulting in separation according to the specific gravity of the photosynthesis-specific cell membrane. Also, since the thylakoid membrane vesicle and the intracytoplasmic membrane vesicle may have a diameter of 1 to 500 nm, and preferably 10 to 200 nm, a size-dependent separation method using various types and shapes of membranes with pores larger or smaller than the diameter of the vesicles may also be a useful alternative.

In the centrifugation using a sucrose density gradient, the sucrose density may be 5 to 50%, and the centrifugation is preferably performed under a sucrose density gradient of 10 to 50% for the thylakoid membrane vesicle, and 5 to 35% for the intracytoplasmic membrane vesicle. When less than the above density range, the specific gravity of sucrose is lower than that of the photosynthetic membrane vesicle, and thus the centrifugation fails. However, when more than the above range, the specific gravity of sucrose may be too high to perform centrifugation.

The centrifugation using the above sucrose density gradient may be performed at 50,000 to 500,000 g for 20 minutes to 24 hours, and for the thylakoid membrane vesicle, preferably at 100,000 to 400,000 g for 1 to 20 hours, and for the intracytoplasmic membrane vesicle, preferably at 60,000 to 200,000 g for 30 minutes to 10 hours. When less than the above range, a typical cell membrane and the photosynthetic membrane vesicle are not separated from each other since they are both present in the upper portion of a supernatant, and when more than the above range, the typical cell membrane and the photosynthetic membrane vesicle are not separated from each other since they are both precipitated.

Purification of high value-added biomaterials such as drugs, health supplementary food, cosmetic ingredients, etc. from living organisms requires very high costs. Accordingly, an attempt has been made to develop a process of directly preparing such useful substances in vitro using synthases and precursors corresponding to the substances. While various enzyme reactions mostly require ATP or NAD(P)H as an energy source, even when ATP or NAD(P)H is chemically synthesized, or regenerated from ADP and NAD(P)$^+$ using a conventionally known enzyme, a substrate becoming an energy source should be continuously provided, and thus the development of a process using such a material required a large cost. According to the method of producing ATP and NAD(P)H provided by the present invention, unlike the conventional methods, ATP and NAD(P)H may be continuously provided using a photosynthetic membrane vesicle under the condition of the application of light, and in this process, an additional electron donor, other than water, is not needed, resulting in the economical production of ATP or NAD(P)H.

Advantageous Effects

In summary, characteristics and advantages of the present invention are as follows:

(1) The present invention provides a composition containing a photosynthetic membrane vesicle to produce a product of the light-dependent reactions in photosynthesis and a method of producing a product of the light-dependent reactions in photosynthesis using the composition.

(2) Also, the present invention provides a method of preparing a light-dependent reaction-performing unit, the method including separating a vesicle from photosynthetic bacteria or algae.

(3) By using the composition according to the present invention, under the condition of application of light, a product of the light-dependent reactions in photosynthesis can be continuously provided with a photosynthetic membrane vesicle, and when a light-dependent reaction-performing unit is constructed with the combination of vesicles from different origins that absorb light at different wavelengths, an output of the product of the light-dependent reactions in photosynthesis can be maximized. The method of producing a product of the light-dependent reactions in photosynthesis according to the present invention does not need an additional electron donor, other than water, resulting in the economical production of ATP and/or NAD(P)H.

DETAILED DESCRIPTION OF THE INVENTION

Modes of the Invention

Figure 1:
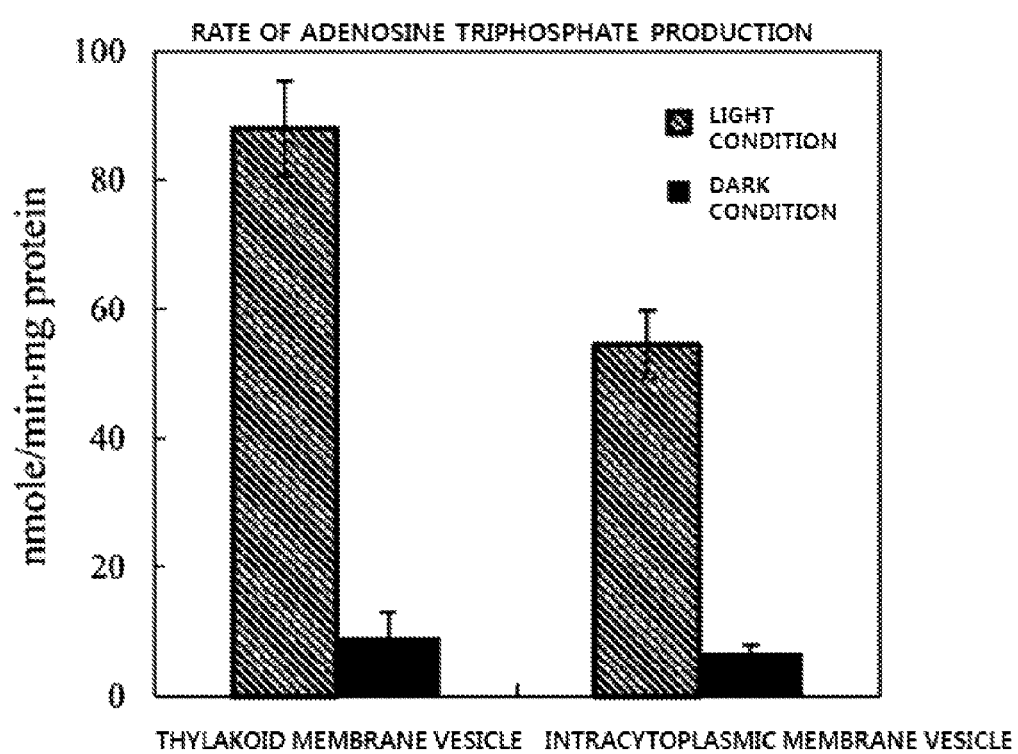
FIG. 1 shows levels of ATP generation investigated under a light-applied condition (light) and a dark condition (dark) using a thylakoid membrane (TM) vesicle or an intracytoplasmic membrane (ICM) vesicle. Under each condition, an ATP production rate was expressed in nmole/min·mg protein.

Hereinafter, the present invention will be described in further detail with reference to examples. There examples are merely provided to explain the present invention in further detail, and therefore, according to the inventive concept, it should be obvious to those of ordinary skill in the art that the scope of the present invention is not limited by the examples.

Example 1: Separation of Thylakoid Membrane Vesicle of Cyanobacteria

To separate a thylakoid membrane vesicle including a light reaction apparatus of cyanobacterium, *Synechocystis* sp. PCC 6803 was used as a target strain. For growth of the strain, partially-modified BG11 minimal medium [18 mM sodium nitrate ($NaNO_3$), 0.23 mM potassium monohydrogen phosphate ($K_2HPO_4$), 0.30 mM magnesium sulfate ($MgSO_4 7H_2O$), 0.24 mM calcium chloride ($CaCl_2.2H_2O$), 31 µM citric acid, 23 µM ferric ammonium citrate, 0.19 mM sodium carbonate ($Na_2CO_3$), 8.8 mM sodium thiosulfate, 46 µM boric acid ($H_3BO_3$), 14 µM manganese chloride ($MnCl_2$), 0.77 µM zinc sulfate ($ZnSO_4 7H_2O$), 1.6 µM sodium molybdate ($Na_2MoO_4 2H_2O$), 0.32 µM copper sulfate ($CuSO_4 5H_2O$), 0.17 µM cobalt nitrate (II) ($Co(NO_3)_2 6H_2O$) (Cratz and Myers. 1955. Am. J. Bot. 42: 282-287)] was used, wherein, for rapid growth of the strain, glucose sterilized using a filter was added to be 10 mM. The *Synechocystis* strain was inoculated into a 300 ml flask containing 50 ml of BG11 minimal medium, and then incubated at 30° C. with shaking at 100 revolutions per minute (rpm) under an aerobic condition. Here, white fluorescent light was used with an intensity of approximately 50 micro Einstein/m²·s. When the optical density of the strain at 600 nm approached approximately 1.0, the strain was inoculated again into a 1 L flask containing 500 ml of BG11 minimal medium and then incubated under the above-described growth condition to have the optical density at 600 nm of approximately 2.0.

Cyanobacteria was cultured under a photosynthesis condition and centrifuged at 4° C. and approximately 7,000 g for 10 minutes to obtain cell pellets, which were suspended in approximately 10 ml of a 10 mM Tris-HCl (pH 7.5) buffer containing 1 mM EDTA and then placed on ice. The suspended cells were disrupted by glass beads, which were added to a buffer containing the cells to be full of the glass beads, followed by vigorously shaking for 2 minutes per each of 5 times (total 10 minutes) to disrupt the cells. Afterward, undisrupted cells, large cell fragments, and the glass beads were discarded after centrifugation at approximately 3,000 g and 4° C. for 10 minutes. Here, a supernatant obtained thereby included various water-soluble cell components and cell membranes (including vesicles), and were centrifuged at 100,000 g for 30 minutes to obtain a total cell membrane. Subsequently, to isolate the thylakoid membrane vesicle from the total cell membrane, the sample was centrifuged with a 10-50% sucrose density gradient at 130,000 g for 15 hours. From layers separated thereby, a part corresponding to 38 to 42% sucrose density was obtained, and concentrated by centrifugation again at 187,000 g for 45 minutes. The membrane vesicle located at the bottom layer after the centrifugation was dissolved in a 10 mM Tris-HCl (pH 7.5) buffer containing 0.25 M sucrose, and then subjected to phase partitioning (Norling et al. 1998. FEBS Lett. 436: 189-192) using dextran T-500 and PEG 3350, thereby obtaining parts showing a green color due to the presence of the thylakoid membrane vesicle of cyanobacteria from the fifth and sixth layers from the bottom.

Example 2: Separation of Intracytoplasmic Membrane Vesicle of Purple Non-Sulfur Bacteria To separate an intracytoplasmic membrane vesicle including a light reaction apparatus of purple non-sulfur bacteria, *Rhodobacter sphaeroides* 2.4.1 (ATCC BAA-808, Cohen-Bazire et al. 1956. J. Cell. Comp. Physiol. 49: 25-68) was used as a target strain, and for growth of the strain, Sistrom's minimal medium [20 mM potassium dihydrogen phosphate ($KH_2PO_4$), 3.8 mM ammonium sulfate (($NH_4)_2SO_4$), 34 mM succinate, 0.59 mM L-glutamate), 0.30 mM L-aspartate, 8.5 mM sodium chloride, 1.05 mM nitrilotriacetic acid, 1.2 mM magnesium chloride ($MgCl_2$ $6H_2O$), 0.23 mM calcium chloride ($CaCl_2$ $7H_2O$), 25 µM ferrous sulfate ($FeSO_4.7H_2O$), 0.16 µM ammonium molybdate (($NH_4)_6Mo_7O_{24}.4H_2O$), 4.7 µM EDTA, 38 µM zinc sulfate ($ZnSO_47H_2O$), 9.1 µM manganese sulfate ($MnSO_4.H_2O$), 1.6 µM copper sulfate ($CuSO_4.5H_2O$), 0.85 µM cobalt nitrate(II) ($Co(NO_3)_2.6H_2O$), 1.8 µM borate ($H_3BO_3$), 8.1 µM nicotinic acid, 1.5 µM thiamine hydrochloride, 41 nM biotin (Sistrom. 1962. J. Gen. Microbiol. 28: 607-616)] was used. The *Rhodobacter sphaeroides* strain was inoculated into a 300 ml flask containing 30 ml of Sistrom's minimal medium and incubated with shaking at 250 rpm and 30° C. under an aerobic condition. When the optical density of the strain at 660 nm reached approximately 1.0, the strain was inoculated into a 1 L transparent container filled up with Sistrom's minimal medium to prevent input of oxygen, and grown under an anaerobic condition using fluorescent light with an intensity of 15 Watts/$m^2$ until an optical density at 660 nm became approximately 2.0.

The *Rhodobacter sphaeroides* cells incubated under the photosynthesis condition were centrifuged at approximately 7,000 g and 4° C. for 10 minutes to obtain cell pellets, which were suspended in approximately 10 ml of a 10 mM Tris-HCl (pH 7.5) buffer containing 1 mM EDTA, and placed on ice. To disrupt the suspended cells, a cell disrupting method using ultrasonic waves (sonication) was performed for 5 minutes per each of four times (total 20 minutes). Afterward, undisrupted cells and large cell fragments were discarded after centrifugation at approximately 10,000 g and 4° C. for 30 minutes. Here, a supernatant obtained thereby included various water-soluble cell components and cell membrane (including vesicles), and to isolate an intracytoplasmic membrane, centrifugation was performed at 96,000 g for 4 hours with a 5 to 35% sucrose density gradient. Subsequently, parts showing a brown color, which contain the intracytoplasmic membrane vesicle containing a photosynthetic apparatus of *Rhodobacter sphaeroides*, were obtained from several layers separated from each other.

Example 3: Confirmation of ATP Generated Using Photosynthetic Membrane Vesicle

The thylakoid membrane vesicle containing the light reaction apparatus of cyanobacteria generated a proton concentration gradient between the inner and outer spaces of the membrane by transferring protons while electrons from water were transported under a light condition, and converted ADP and inorganic phosphate into ATP by the action of ATP synthase using kinetic energy derived from the proton concentration gradient as a driving force. Likewise, in reaction centers of *Rhodobacter sphaeroides*, a photochemical reaction by light energy was induced, resulting in induction of cyclic electron transfer, and ATP synthesis by ATP synthase using the proton concentration gradient generated thereby as a driving force. Accordingly, in this example, to investigate whether the separated thylakoid membrane vesicle and intracytoplasmic membrane vesicle had an activity of performing a light-dependent reaction under the light condition, ATP synthesis efficiency was tested. The ATP synthesis efficiency may be assessed by various methods that can selectively detect ATP (generally using an ATP quantification method performed on a final product having an optical density with respect to a specific wavelength or exhibiting fluorescence, which is generated by an enzyme reaction consuming ATP and converting a transparent substrate with the ATP as a driving force), and an optimal method for evaluating the efficiency may be determined by one of ordinary skill in the art according to the purpose of research and development. In this example, as a method for quantifying ATP, an ATP assay kit (BioVision) was used.

A reaction was performed using a 50 mM PBS buffer (phosphate buffered saline, pH 7.4) at 30° C. while ADP was added as a substrate to a concentration of 1 mM. Levels of proteins respectively containing the thylakoid membrane vesicle and the intracytoplasmic membrane vesicle were quantified, thereby determining concentrations of the proteins. Values of ATP production rates measured several times were normalized to a concentration of the protein contained in each of the two types of cell membrane vesicles. A degree of ATP synthesis was assessed by a change in optical density at 570 nm, and a standard curve was plotted through an experiment performed as described above using various concentrations of ATP, and thereby the measured value of the optical density can be converted into an amount of ATP generation. The amount of ATP production determined thereby was expressed as a value over time, and the ATP production rate was expressed as nmole ATP-generating values per unit protein and per minute. FIG. 1 shows ATP synthesis efficiency by the thylakoid membrane vesicle and intracytoplasmic membrane vesicle determined by the above-described method. Both of the cell membrane vesicles exhibited considerably lower ATP synthesis rates under a dark condition in which light was not applied than those under the light condition in which light was applied, and from this result, it can be considered that most of ATP generated in this example were products of the light-dependent reaction in photosynthesis. In this example, to measure the ATP synthesis efficiency of the thylakoid membrane vesicle, fluorescent light with an intensity of 50 micro Einstein/$m^2$·s was used, to assess ATP synthesis efficiency of the intracytoplasmic membrane vesicle, incandescent light with an intensity of 15 Watts/$m^2$ was used.

Example 4: Experiment on Efficiency of ATP Generation According to Concentration of Photosynthetic Cell Membrane Vesicle Optimal concentrations of the thylakoid membrane vesicle and the intracytoplasmic membrane vesicle to produce ATP by a light-dependent reaction were to be determined. To this end, the separate thylakoid membrane vesicle and intracytoplasmic membrane vesicle were prepared at various concentrations, and ATP synthesis rates were measured in the same manner as described in Example 3. In this example, the thylakoid membrane vesicle was quantified based on the concentration of chlorophyll a, and the intracytoplasmic membrane vesicle was quantified based on the concentration of bacteriochlorophyll a. A part of the separated thylakoid membrane vesicle or intracytoplasmic membrane vesicle was extracted with a mixed solvent containing acetone and methanol (in a ratio of 7:2), resulting in extraction of the chlorophyll a or bacteriochlorophyll a, which is a pigment, from the vesicle. Here, optical densities were measured at approximately 660 nm for the chlorophyll a and at approximately 780 nm for the bacteriochlorophyll a, and applied to the standard curve plotted with the previously-known concentration of chlorophyll a or bacteriochlorophyll a, and the concentration of the separated thylakoid membrane vesicle or intracytoplasmic membrane vesicle was assessed.

Figure 2:
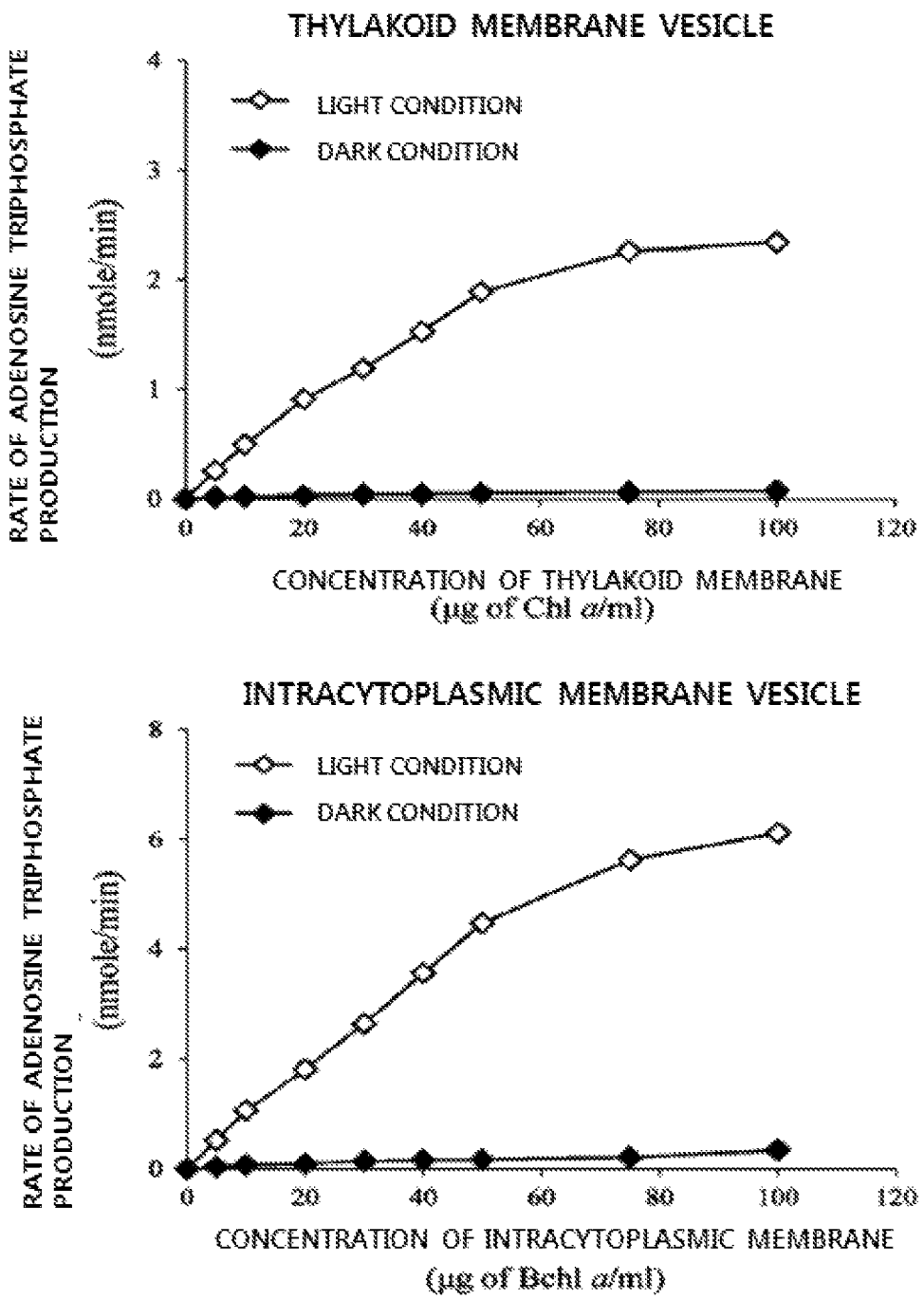
FIG. 2 shows ATP production rates investigated under a light-applied condition (light) and a dark condition (dark) using a thylakoid membrane (TM) vesicle or an intracytoplasmic membrane (ICM) vesicle. The drawing on the upper panel shows the ATP production rate using the thylakoid membrane vesicle, and the drawing on the lower panel shows the ATP production rate using the intracytoplasmic membrane vesicle. Concentrations of the thylakoid membrane vesicle and the intracytoplasmic membrane vesicle were determined by concentrations of chlorophyll a (Chl a) and bacteriochlorophyll a (Bchl a), respectively. Under each concentration condition, the ATP production rate was expressed in nmole/min.

FIG. 2 shows ATP synthesis efficiency according to the concentrations of the thylakoid membrane vesicle and intracytoplasmic membrane vesicle determined by the above-described method. As a result, both of the cell membrane vesicles showed increased ATP synthesis rates according to the increase in concentrations under the light condition, and low degrees of ATP synthesis under the dark condition. In the thylakoid membrane vesicle, the ATP synthesis rate was saturated at a concentration of approximately 80 µg chlorophyll a/ml, and in the intracytoplasmic membrane vesicle, similarly, the ATP synthesis rate was saturated at a concentration of approximately 100 µg bacteriochlorophyll a/ml. This result shows that in the presence of a high concentration of a photosynthetic apparatus, the photosynthetic apparatus absorbs light, thereby decreasing light permeability, and therefore, the use of the photosynthetic membrane vesicle at the suitable concentration or more may be inefficient. As light intensity is increased, an optimal concentration of the added photosynthetic membrane vesicle may also be increased, by taking the conditions for providing light energy into consideration, a concentration of the photosynthetic membrane vesicle used herein may be determined by those of ordinary skill in the art according to the purpose of research and development.

Figure 3:
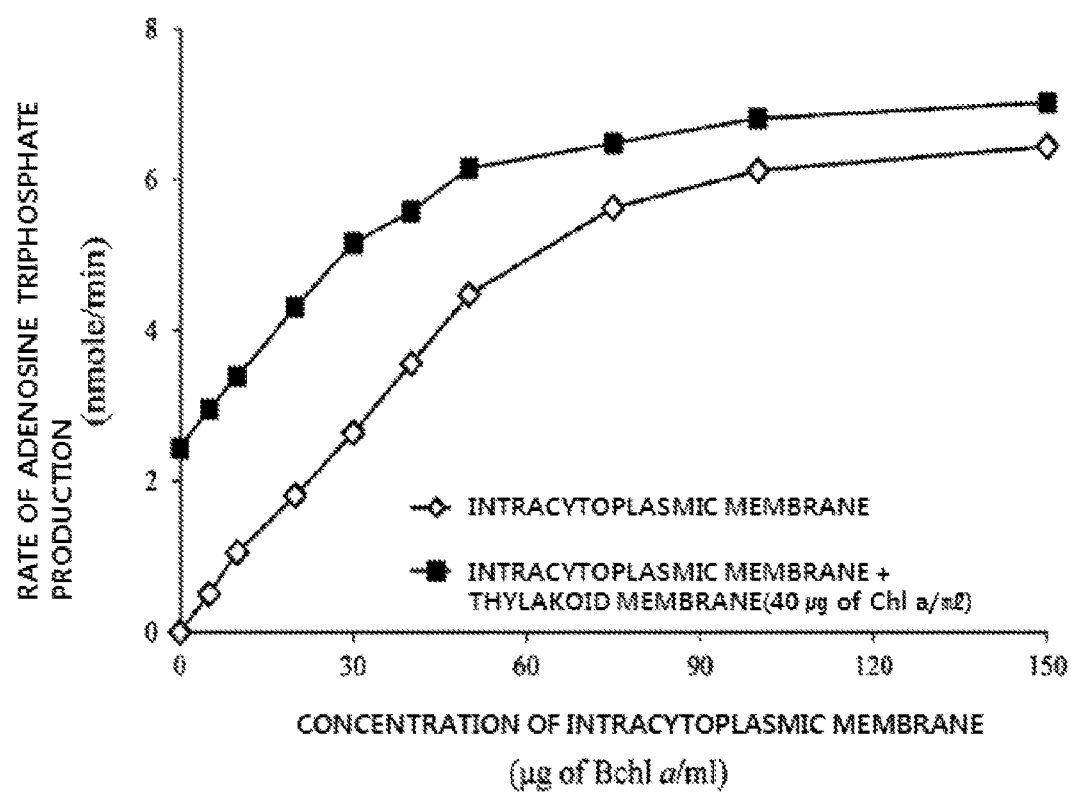
FIG. 3 shows the improvement of ATP production efficiency when the thylakoid membrane vesicle and the intracytoplasmic membrane vesicle, which have different absorption wavelengths, are used together. Concentrations of the thylakoid membrane (TM) vesicle and the intracytoplasmic membrane (ICM) vesicle were determined by concentrations of chlorophyll a (Chl a) and bacteriochlorophyll a (Bchl a), respectively. Under two conditions in which the thylakoid membrane (TM) vesicle was not used, or used at a fixed concentration of 40 µg Chl a/ml, varying concentrations of the intracytoplasmic membrane (ICM) vesicles were added, and then the ATP production rates were measured when using incandescent light in a wide range of wavelengths at an intensity of 15 Watts/m², and the values were expressed in nmole/min.

Example 5: Experiment on Efficiency of ATP Generation Using Two Types of Photosynthetic Cell Membrane Vesicles with Different Absorption Wavelengths The thylakoid membrane vesicle absorbs a short wavelength, which is shorter than and around the wavelength of 660 nm, but the intracytoplasmic membrane vesicle directly uses light energy at wavelength in a range of 800 to 900 nm in photosynthesis. Accordingly, when the two types of photosynthetic membrane vesicles were used at the same time to induce the light-dependent reaction, they will absorb light energy respectively at corresponding wavelengths, and thus one vesicle will not affect the photosynthesis efficiency of the other. Therefore, it was expected that ATP can be synthesized in a limited space with relatively higher efficiency. To confirm this, while the concentration of the separated thylakoid membrane vesicle was fixed, the intracytoplasmic membrane vesicle was added at varying concentrations, followed by measuring an ATP synthesis rate using the same method as described in Example 3. To simultaneously measure the ATP synthesis efficiency of the two types of photosynthetic membrane vesicles, incandescent light having a wide wavelength range of a light source was applied at an intensity of 15 Watts/m$^2$. FIG. 3 shows ATP synthesis efficiency measured when ATP is produced only using the thylakoid membrane vesicle and when ATP is produced using the thylakoid membrane vesicle and the intracytoplasmic membrane vesicle together. From the conditions in which the concentration of the intracytoplasmic membrane vesicle is beyond 60 to 80 µg bacteriochlorophyll a/ml, the ATP synthesis rate is no longer increased according to the concentration of the added photosynthetic apparatus, and thus its value was saturated. However, under all the concentrations at which the ATP synthesis rate is not saturated and saturated, an experiment was conducted by the addition of the two types of photosynthetic membrane vesicles, resulting in relatively higher ATP synthesis efficiency. This result shows that the two types of photosynthetic membrane vesicles absorb light at different wavelengths. Moreover, when the saturation of the ATP synthesis rate is saturated by the use of a high concentration of either one of the photosynthetic membrane vesicles, the two types of photosynthetic membrane vesicles can be used together, thereby synthesizing ATP with higher efficiency.

Example 6: Experiment on Reduction of NADP Using Thylakoid Cell Membrane Vesicle The electron flow taking place in the thylakoid membrane vesicle during light irradiation is transferred to ferredoxin, and finally generates NADPH by reduction of NADP$^+$. The NADPH generated thereby may be converted into NADH by the action of pyridine nucleotide transhydrogenase (Pnt) expected to be present in the cell membrane vesicle. Such NADH and NADPH are necessarily required for various types of biosynthesis in vivo, and have become critical products of the light-dependent reactions in photosynthesis as well as ATP. Accordingly, in this example, to investigate whether the separated thylakoid membrane vesicle also enables reduction to NADH and NADPH as well as ATP synthesis activity under a light condition, efficiency of reduction to NADH and NADPH was assessed. The efficiency of reduction to NADH and NADPH may be assessed by various methods capable of selectively detecting the two substances (mostly by using a method of quantifying NADH and NADPH by oxidizing NADH and NADPH to induce an enzyme reaction for converting a transparent substrate using the oxidized substances as a driving force, resulting in a final product having an optical density with respect to a specific wavelength or fluorescence, and then measuring the final product), and the optimal method can be determined by those of ordinary skill in the art depending on the purpose of research and development. In this example, as the method of quantifying NADH and NADPH, an NADH assay kit (BioVision) and an NADPH assay kit (BioVision) were used. Both types of kits were used to selectively measure NADH and NADPH.

Figure 4:
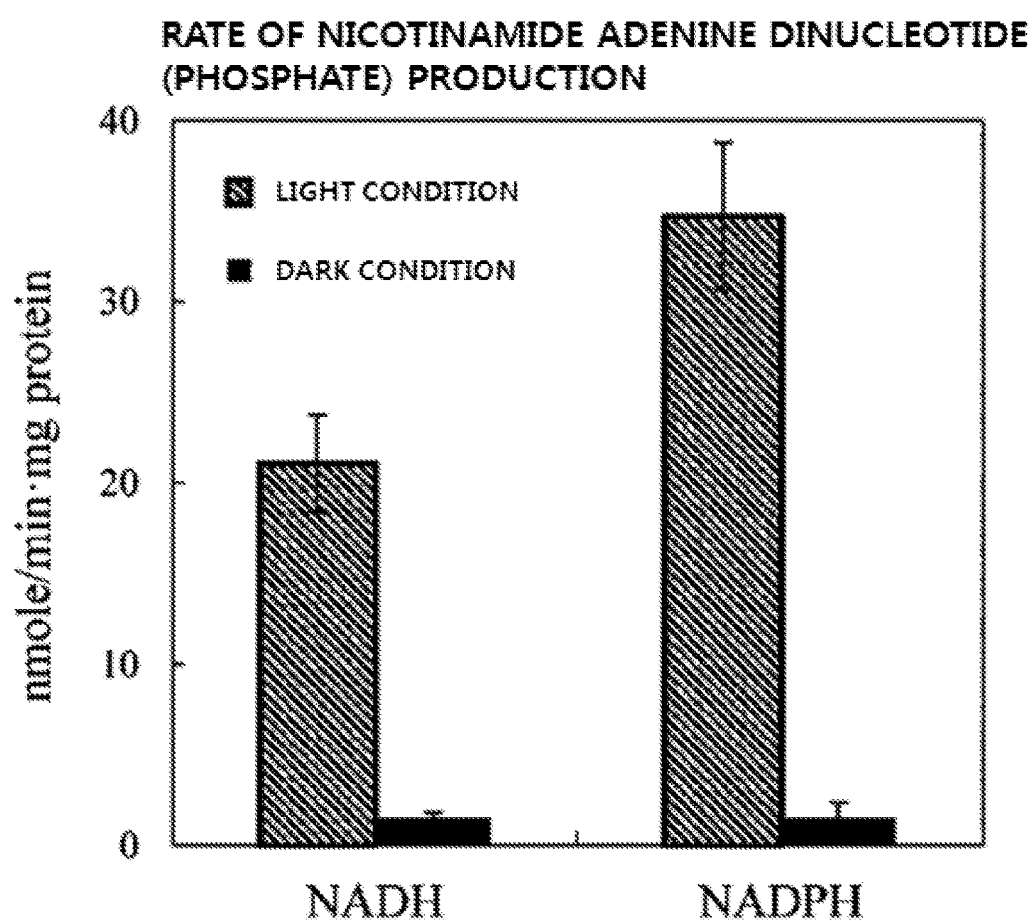
FIG. 4 shows the efficiency of reducing $NAD^+$ and $NADP^+$ under the light condition and the dark condition using a thylakoid membrane vesicle. NADH and NADPH production rates were expressed in nmole/min·mg protein.

A reaction was conducted with a 50 mM PBS buffer (phosphate buffered saline, pH 7.4) and a solution containing 1 mM NAD and 1 mM NADP as substrates at 30° C. To assess NADPH synthesis efficiency, only NADP$^+$ was added to a reaction solution, but to assess NADH synthesis efficiency, both of NAD$^+$ and NADP$^+$ were added thereto. By using the quantification of a protein contained in the thylakoid membrane vesicle used herein, the protein concentration was determined, and values obtained by several measurements were normalized to a value of the concentration of the protein contained in the thylakoid membrane vesicle. A degree of NADH and NADPH synthesis was assessed by a change in optical density at 450 nm, and a standard curve was plotted through an experiment performed as described above using various concentrations of NADH and NADPH, and thereby the measured value of the optical density can be converted into amounts of NADH and NADPH generation. The amounts of NADH and NADPH generation determined thereby were expressed as values over time, and the NADH and NADPH production rates were expressed as nmole values of NADH and NADPH produced per minute. FIG. 4 shows NADH and NADPH synthesis efficiency using the thylakoid membrane vesicle determined by the above-described method by applying fluorescent light with an intensity of 50 micro Einstein/m$^2$·s. As a result, the NADH and NADPH synthesis rates under the dark condition in which light is not applied were considerably lower than those under the light condition, and from this result, it can be considered that most of NADH and NADPH generated in this example were products of the light-dependent reaction in photosynthesis using the light. As a result, the NADPH production efficiency was higher than that of NADH, and thus the method of generating a light-dependent reaction product using the thylakoid membrane vesicle may be useful to induce a biosynthetic reaction that consumes ATP or NADPH. However, from the result shown in FIG. 4, it was also identified that a considerable level of NADH is also generated by the action of a nucleotide transhydrogenase, and may also be employed to induce biosynthesis consuming NADH by using the activity of the nucleotide transhydrogenase present in the thylakoid membrane vesicle.

Example 7: Experiment on Reduction of NADP Using Intracytoplasmic Membrane Vesicle When, other than the photophosphorylation for generating ATP, reverse electron flow takes place in the intracytoplasmic membrane vesicle, succinate is converted into fumarate by the action of succinate dehydrogenase, which is complex II, and NAD is reduced into NADH by complex I. NADH generated thereby may be converted into NADPH by the action of pyridine nucleotide transhydrogenase (Pnt) like in the oxygenic photosynthesis. Accordingly, in this example, to confirm that the separated intracytoplasmic membrane vesicle enables reduction to NADH and NADPH as well as ATP synthesis activity under the light condition, the efficiency of reduction to NADH and NADPH was assessed by the method described in Example 6.

Figure 5:
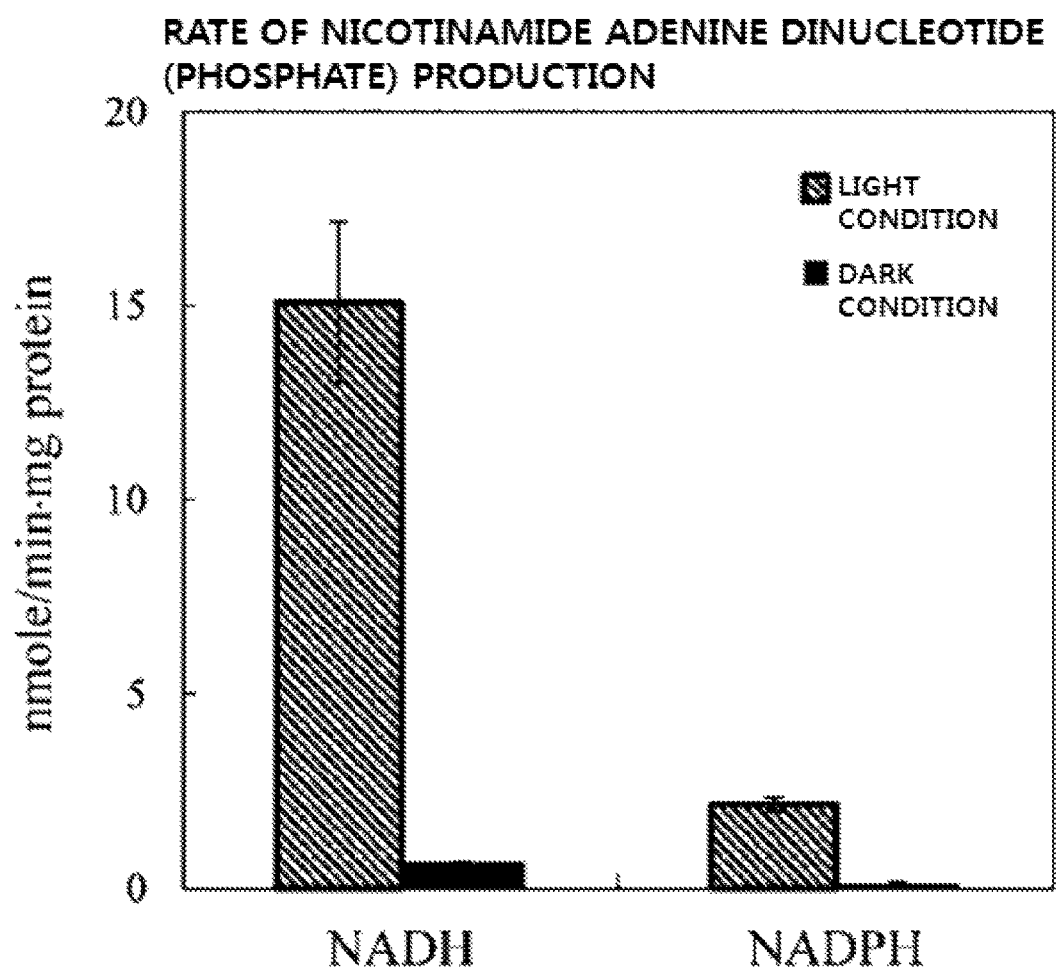
FIG. 5 shows efficiency of reducing $NAD^+$ and $NADP^+$ under the light condition and the dark condition using an intracytoplasmic membrane vesicle. NADH and NADPH production rates were expressed in nmole/min·mg protein.

A reaction was conducted with a 50 mM PBS buffer (phosphate buffered saline, pH 7.4) and a solution containing 1 mM NAD and 1 mM NADP as substrates at 30° C. Unlike Example 6, 5 mM succinate was further added as an electron donor. To assess NADH synthesis efficiency, only NAD$^+$ was added to a reaction solution, but to assess NADPH synthesis efficiency, both of NAD$^+$ and NADP$^+$ were added thereto. By using the quantification of a protein contained in the intracytoplasmic membrane vesicle used herein, the protein concentration was determined, and values obtained by several measurements were normalized to a value of the concentration of the protein contained in the intracytoplasmic membrane vesicle. FIG. 5 shows NADH and NADPH synthesis efficiency using the intracytoplasmic membrane vesicle determined by the above-described method by applying incandescent light at an intensity of 50 micro Einstein/m$^2$·s. As a result, similar to Example 6, NADH and NADPH synthesis rates under the dark condition in which light is not applied were considerably lower than those under the light condition, and from this result, it can be considered that most of NADH and NADPH generated in this example were products of the light-dependent reactions in photosynthesis using the light. Contrarily, in the intracytoplasmic membrane vesicle, different from the result shown in Example 6, the NADH production efficiency was considerably higher than that of NADPH, and thus the method of generating a light-dependent reaction product using the intracytoplasmic membrane vesicle may be useful to induce a biosynthetic reaction that consumes ATP or NADH. However, it was also identified that a considerable level of NADPH is also generated by the action of a nucleotide transhydrogenase, and therefore, the NADPH production efficiency can also be improved by various additional attempts to increase the activity of nucleotide transhydrogenase.

Moreover, a method of improving the NADH and NADPH synthesis efficiency using the thylakoid membrane vesicle and intracytoplasmic membrane vesicle together, each using light energy having different wavelength range, has not been described in detail, but may be easily achieved by those of ordinary skill in the art with reference to the method of improving the ATP synthesis efficiency using the thylakoid membrane vesicle and the intracytoplasmic membrane vesicle together, described in Example 5.

Hereinafter, exemplary embodiments of the present invention will be described in detail. The present invention can be modified and implemented in various forms, and therefore, only specific embodiments will be described in detail. However, the present invention is not limited to specific disclosures, and it should be understood that the present invention includes all modifications, equivalents and alternatives included in the technical idea and scope of the present invention.

The invention claimed is:

1. A composition for producing a product of the light-dependent reactions in photosynthesis, comprising a mixture of:
   a) a photosynthetic vesicle separated from a membrane, wherein the membrane is the intracytoplasmic membrane (ICM) of a purple non-sulfur bacterium; and
   b) a vesicle separated from the thylakoid membrane of a cyanobacterium or alga.

2. The composition of claim 1, wherein the product of the light-dependent reactions in photosynthesis is a composition comprising adenosine triphosphate (ATP), nicotinamide adenine dinucleotide (NADH) and reduced nicotinamide adenine dinucleotide phosphate (NADPH).

3. The composition of claim 1, wherein the purple non-sulfur bacterium is a *Rhodobacter* sp.

4. The composition of claim 1, wherein the vesicle separated from the thylakoid membrane of the cyanobacterium or alga and the vesicle separated from the intracytoplasmic membrane of the purple non-sulfur bacterium absorb light in mutually different wavelength ranges.

5. The composition of claim 4, wherein the light in the mutually different wavelength bands is visible light and infrared light.

6. The composition of claim 1, wherein the thylakoid membrane of the cyanobacterium or alga includes chlorophyll a (Chl a) in a concentration of 1 μg chlorophyll a/ml to 1 mg chlorophyll a/ml.

7. The composition of claim 1, wherein the vesicle separated from the intracytoplasmic membrane of the purple non-sulfur bacterium includes bacteriochlorophyll a (Bchl a) in a concentration of 1 μg bacteriochlorophyll a/ml to 1 mg bacteriochlorophyll a/ml.

8. The composition of claim 1, wherein the vesicle separated from the thylakoid membrane of the cyanobacterium or alga and the vesicle separated from the intracytoplasmic membrane of the purple non-sulfur bacterium have a diameter of 1 to 500 nm.

9. A method of producing a product of the light-dependent reactions in photosynthesis using the composition of claim 1, the method comprising:
 a)
  preparing a light-dependent reaction-performing unit by placing the composition of claim 1 inside the unit; and
 b) applying light to the light-dependent reaction-performing unit.

10. The method of claim 9, wherein the product of the light-dependent reactions in photosynthesis is one or more light reaction products selected from the group consisting of adenosine triphosphate (ATP), nicotinamide adenine dinucleotide (NADH) and nicotinamide adenine dinucleotide phosphate (NADPH).

11. The method of claim 10, wherein the NADH is able to be converted into NADPH without additional enzyme treatment.

12. The method of claim 10, wherein the NADPH is able to be converted into NADH without additional enzyme treatment.

13. The method of claim 9, wherein the light has a wavelength in the visible or infrared range.

14. A method of manufacturing the photosynthetic light-reaction-performing composition of claim 1, comprising:
 a) separating a vesicle from a thylakoid membrane of a cyanobacterium or alga;
 b) separating a vesicle from the intracytoplasmic membrane of a purple non-sulfur bacterium; and
 c) combining the vesicles made in (a) and (b).

15. The method of claim 14, wherein the separating of the vesicle from the membrane includes:
 a) preparing a cell lysate by disrupting the cyanobacterium, alga or purple non-sulfur bacterium; and
 b) separating the vesicle from the membrane contained in the cell lysate by centrifugation in a sucrose density gradient.

16. The method of claim 15, wherein the disruption is performed using glass beads or ultrasonic waves.

17. The method of claim 15, wherein the sucrose density is 5 to 50%.

18. The method of claim 15, wherein the centrifugation is performed at 50,000 to 500,000 g for 20 minutes to 24 hours.

* * * * *